United States Patent [19]
Allen et al.

[11] Patent Number: 5,760,009
[45] Date of Patent: *Jun. 2, 1998

[54] SPIROSTANYL GLYCOSIDAL CRYSTALLINE MONOHYDRATE

[75] Inventors: Douglas J. M. Allen, New London; Harry A. Watson, Jr., Groton; Jonathan B. Zung, East Lyme, all of Conn.

[73] Assignee: Pfizer Inc., New York, N.Y.

[*] Notice: The term of this patent shall not extend beyond the expiration date of Pat. No. 5,629,295.

[21] Appl. No.: 532,571

[22] PCT Filed: Jan. 19, 1994

[86] PCT No.: PCT/US94/00446

§ 371 Date: Oct. 19, 1995

§ 102(e) Date: Oct. 19, 1995

[87] PCT Pub. No.: WO94/25479

PCT Pub. Date: Nov. 10, 1994

Related U.S. Application Data

[63] Continuation of Ser. No. 54,449, Apr. 28, 1993, abandoned.
[51] Int. Cl.$^6$ .............................. A61K 31/70; C07H 15/24
[52] U.S. Cl. .............................. 514/26; 536/6; 536/6.1; 536/18.5
[58] Field of Search .............................. 536/4.1, 8.1, 6, 536/17.2, 6.1, 5; 517/26

[56] References Cited

U.S. PATENT DOCUMENTS

| | | | |
|---|---|---|---|
| 4,260,603 | 4/1981 | Pegel et al. | 514/26 |
| 4,265,886 | 5/1981 | Pegel et al. | 514/26 |
| 4,461,762 | 7/1984 | Malinow | 514/26 |
| 4,602,003 | 7/1986 | Malinow | 514/26 |
| 4,602,005 | 7/1986 | Malinow | 514/26 |
| 5,010,185 | 4/1991 | Urban | 536/6.1 |
| 5,502,948 | 4/1996 | Matsumurc et al. | 536/5 |
| 5,530,107 | 6/1996 | Douglas et al. | 536/6.1 |
| 5,629,295 | 5/1997 | Deninno et al. | 514/26 |

FOREIGN PATENT DOCUMENTS

| | | |
|---|---|---|
| 0020029 | 2/1979 | European Pat. Off. |
| 9307167 | 4/1993 | WIPO |
| 9311150 | 6/1993 | WIPO |
| 9400480 | 6/1994 | WIPO |

OTHER PUBLICATIONS

"Steroidal Glycosides XXII; Rockogenin Glycosides." Kintya, P.K.; Bobeiko, V.A. Khim. Prir. Soedin, (1) 102–103, 1979.

"Hemolytic Properties of Synthetic Glycosides," Segal, R.; Shud, F.; Milo–Goldzweigh, I.J. Pharm. Sci. 67(11) 1589 1592, 1978.

"Saponins in the Leaves of Agrave Americana." Kintya, P.K.; Bobeiko, V.A.; Krokhmalyuk, V.V.; Chirva, V. Ya. Pharmazie 30(6), 396–7, 1975.

"Steriod Glycosides of the Roots of Capsicum Annuum II: The Structure of the Capsicosides" Gutsu, E.V.; Kintya, P.K.; Lazurevskii, G.V.; Khim. Prir. Soedin. (2), 242–246, 1987.

"Steroidal Saponins from a Cultivated form of Agava Sisalana" Ding, Y.; Chen, Y.Y.; Wang, D.Z.; Yang, C.R. Phytochemistry 28(1), 2787–91, 1989.

"Novel Silver Salts in Glycoside Synthesis" Wulff, G.; Rohlek, G.; Kruger, W. Chem. Ber. 105, 1097–1110, 1972.

The Susceptibility of Cholesterol–Depleted Erythrocytes to Saponin and Sapogenin Hemolysis Segal R.; Milo–Golzweigh, I. Biochem. Biophys. Acta 512, 223–226, 1978.

"Steriod Saponins III: Glycosides A and B from Yucca Filamentosa" Kintya, P.K.; Dragelin, I.P.; Chirva, V. Ya. Khim. Prior. Soedin. (5), 615–16, 1972.

Steroidal Glycosides of Tribulus Terrestirs Linn. Mahato, S.B.; Sahu, N.P.; Ganguly, A.N.; Miyahara, K.; Kawasaki, T.J. Chem. Soc. Perkin Trans. 1 2405–2410, 1981.

"Structural Features of the Antioxidant and Fungicidal Activity of Steriod Glycosides" Dimoglo, A.S.; Choban I.N.; Bersuker, I.B.; Kintya, P.K.; Balashova, N.N. Bioorg. Khim. 11(3), 408–413, 1985.

"Two New Steroidal Glucuronides From Solanum Lyratum; II" Yahara, S.; Morooka, M.; Ikeda, M.; Yamasaki, M.; Nohara, T. Planta Med. (6), 496–8, 1986.

"Preparation and Properties of Some New Steroid Beta–D–Glucopyranosides, Beta–D–Glucopyranosiduronic Acids, and Derivatives" Schneider, J.J. Carb. Research 17, 199–207, 1971.

"Structure Activity Relationships in Steroid Glycosides" Dimolgo, A.S.; Choban, I.N.; Bersuker, I.B.; Kintya, P.K.; Khim. Far., Zh. 19(2), 185–9, 1985.

"Modifiers of Bilayer Lipid Membranes among Steroid Glycosides" Bogatskii, A.V.; Nazarova, N. Yu.; Kintya, P.K.; Bobeiko, V.A. Dokl. Akad. Nauk. SSSR[Biophys] 252(1), 235–7, 1980.

"Steriodal Saponins from Several Species of Liliiflorae Plants" Yang, C.; Li, K.; Ding, Y. Yunnan Ahiwu Yuanjiu Zengkan, Suppl. 3, 13–23, 1990.

"Search for Hypocholesterolemic Agents Among Steriod Glycodies" Kintya, P.K.; Vasilenko, I.K.; Gorianu, G.M.; Bobeiko, V.A.; Suetina, I.V.; Mashchenko, N.E. Kim. Farm. Zh. 15(9), 55–60, 1981.

"Steriod Glycosides from the Leaves of Agave Americana" G.V.; Bobeiko, V.A.; Kintya, P.K. Dokl. Akad. Nauk. SSSR 224(6), 1442–4, 1975.

"Steriod Glycosides form Asparagus Officinalis" Lazurevskii, G.V.; Goryanu, G.M.; Kintya, P.K. Dokl. Akad. Nauk. SSSR 231(6), 1479–81, 1976.

(List continued on next page.)

Primary Examiner—Elli Peselv
Attorney, Agent, or Firm—Peter C. Richardson; Gregg C. Benson; A. Dean Olson

[57] ABSTRACT

A crystalline monohydrate of (3β,5α,25R)-3-[(β-D-cellobiosyl)oxy]spirostan-11-one that is useful as a hypocholesterolemic or antiatherosclerosis agent.

6 Claims, 1 Drawing Sheet

OTHER PUBLICATIONS

"Steriod Saponins XVII; The structure of Asparagosides D and G." Goryanu, G.M.; Kintya, P.K. Khim. Prir. Soedin, (6), 762–765, 1976.

"The Structure of the Glycosides of Asparagus Officinalis, the Structure of Asparagosides A and B." Goryanu, G.M.; Krokhamlyuk, V.V.; Kintya, P.K. Khim. Prir. Soedin. (3), 400–1, 1976.

"Determination of the Absolute Configuration of a Secondary Hydroxy Group in a Chiral Secondary Alcohol Using Glycosidation Shifts in Carbon–13 NMR Spectroscopy" Seo. S.; Tomita, Y.; Tori, K.; Yoshimura, Y.J. Am. Chem. Soc. 100(11), 3331–3339, 1978.

"Glycosidation Shifts in Carbon–13 NMR Spectroscopy: Carbon–13 Signal from Agylcone and Glucose to Glucoside" Tori, K.; Yoshimura, Y.; Arita, H.; Tomita, Y. Tetrahedr. Lett. (2), 179–182, 1977.

"Chemistry of Ayurvedic Crude Drugs: Part VIII–Shatevari–2: Structure Elucidation of Bioactive Shatavarin–1 and Other Glycosides" Joshi, J.; Dev. S. Ind. J. Chem. 27B, 12–16. 1988.

"Molluscicidal Saponins from Cornus Florida L." Hostettmann, K.; ostettmann–Kaldas, M.; Nakanishi, K. Helv. Chim. Acta 61, 1990–1995, 1978.

"Carbon–13 NMR Spectroscopy of Steroidal Sapogenins" Agrawal, P.K.; Jain, D.C.; Gupta, R.K. Thakur, R.S. Phytochemistry 24(11), 2479–2496, 1985.

"Studies on the Constituents of Asparagi Radix. I. On the Structures of Furostanol Oligosides of Asparagus Cochinchinensis Merrill" Konishi, T.; Shoji, J. Chem. Pharm. Bull. 27(12), 3086–3094, 1979.

"Saponins of the Sprirostanol Series. XII. Parillin, a Saponin with a Highly branched Sugar Chain." Tschesche, R.; Kottler, R.; Kottler, R.; Wulff, G. Just. Liebigs Ann. Chem. 699, 212–22, 1966.

"Damaging Effects of Saponins on Territes" Tschesche, R.; Wulff, G.; Weber, A.; Schmidt, H.Z. Naturforsch. B 25(9) 999–1001, 1970.

"Medicinal Asparagus (Asparagus Officinalis L.) as a Source of steroidal Glycosides" Goryanu, G.M.; Krokhmalyuk, V.V.; Kinty, P.K.; Glyzin. V.L. Farmatsiya (Moscow) 25(4), 66–7, 1976.

Chapman et al. *Studies in the Synthesis of Cortison* (Part XVI) pp. 4344–4350, 1956).

Freire et al. *Chromatography in Biochemistry, Medicine and Environmental Research* vol. vol. 1, pp. 249–259, 1983.

Woo et al. *J. of Natural Products*, vol. 55(8), pp. 1129–1135, (1992).

Tsung et al. *Hua Hsueh Hseuh Pao*, vol. 34(3), pp. 179–196, (1976) Abstract Only.

SPIROSTANYL GLYCOSIDAL CRYSTALLINE MONOHYDRATE

This application was filed under 35 U.S.C. §371 based on PCT/US94/00446, which was filed on Jan. 19, 1994 which is a continuation of U.S. application Ser. No. 08/054,449 which was filed on Apr. 28, 1993 and is now abandoned.

BACKGROUND OF THE INVENTION

This invention relates to steroidal glycosides and methods of using the same, particularly as hypocholesterolemic agents and antiatherosclerosis agents, in mammals.

Many known products possessing hypocholesterolemic activity are cross-linked synthetic polymer derivatives, for example of polystyrene. For example, cross-linked, water-insoluble, bile-acid-binding polystyrene-based resins, e.g., Cholestyramine® agents, have a gritty "mouth-feel", and thus have poor palatability. In addition, these resin beads typically have a low in vivo efficiency. Thus, the effective hypocholesterolemic dose of these materials is excessive, typically 18–24 grams of formulated product per day. Other known polymers having hypocholesterolemic activity include the natural product chitosan and chitosan derivatives as described in European Application pub. no. 0212145. However, the effective hypocholesterolemic dose of these materials is also high.

Other known hypercholesterolemia controlling agents include plant extracts such as "alfalfa saponins". However, these plant extracts are of variable composition and contain significant amounts of nonuseful chemical substances. Due to the variations in composition, it is difficult to set a standard dosage or predict the impurities present. Thus, such extracts are not well suited for use by humans. Further, purification of these extracts would be expensive. As an alternative, certain synthetically produced, pure "sapogenin-derived" compounds, e.g., substances compounded from spirostane, spirostene or sterol-derived compounds, depress cholesterol absorption more effectively than alfalfa extracts on a weight basis and thus can be administered in reasonable sized doses. Because the chemical compositions of these substances are known and because they can be synthesized at a high degree of purity, they are suitable for use by any warm-blooded animal, including humans.

However, unless administered in massive amounts, pure sapogenins do not significantly inhibit cholesterol's absorption. It is only when compounded with another moiety that sapogenins have the desired effect. Examples of such sapogenin compounds are compounds of tigogenin and diosgenin, particularly glycosides thereof. P. K. Kintia, Iu. K. Vasilenko, G. M. Gorianu, V. A. Bobeiko, I. V. Suetina, N. E. Mashchenko, Kim. Pharm. Zh., 1981, 15(9), 55 discloses 3-O-(β-D-galactopyranosyl)hecogenin and its use as a hypocholesterolemic agent. U.S. Pat. Nos. 4,602,003 and 4,602,005 disclose certain steroidal glycosides, in particular 3-O-(β-D-glucopyranosyl)tigogenin and 3-O-(β-D-cellobiosyl)tigogenin and their use for the control of hypercholesterolemia. 3-O-(β-D-cellobiosyl)tigogenin has superior hypocholesterolemic activity when compared to, for example, cholestyramine.

In addition, certain other steroidal glycosides described below have been published, however these publications do not address hypocholesterolemic activity. "Structural Features of the Antioxidant and fungicidal Activity of Steroid Glycosides", Dimoglo, A. S.; Choban I. N.; Bersuker, I. B.; Kintya, P. K.; Balashova, N. N.; Bioorg. Khim, 11(3), 408–413, 1985 discloses rockogenin β-D-galactopyranoside and tigogenin β-D-lactoside. "Preparation and Properties of Some New Steroid β-D-Glucopyranosides, β-D-Glucopyranosiduronic Acids, and Derivatives", Schneider, J. J.; Carb. Research, 17, 199–207, 1971 discloses tigogenin β-D-glucopyranuronoside. "Sterol Glycoside with Activity as Prostaglandin Synthetase Inhibitor", Pegel, K. H. Walker, H.; U.S. Pat. No. 4,260,603, Apr. 7, 1981 discloses hecogenin β-D-glucopyranoside. "Hemolytic Properties of Synthetic Glycosides", Segal, R.; Shud, F.; Milo-Goldzweig, I.; J. Pharm. Sci., 67 (11) 1589–1592, 1978 discloses tigogenin β-D-maltoside, tigogenin β-L-fucopyranoside, smilagenin β-maltoside and tigogenin α-L-rhamnoside. "Steroid Glycosides from the Roots of Capsicum Annuum II: The Structure of the Capsicosides", Gutsu, E. V.; Kintya, P. K.; Lazurevskii, G. V.; Khim. Prir. Soedin., (2), 242–246, 1987 discloses tigogenin α-D-arabanopyranoside and tigogenin β-D-galactopyranoside. "Molluscicidal Saponins from Cornus Florida L.", Hostettmann, K.; Hostettmann-Kaldas, M.; Nakanishi, K.; Helv. Chim. Acta, 61, 1990–1995, 1978 discloses smilagenin β-D-galactopyranoside. "Steroidal Saponins from Several Species of Liliiflorae Plants", Yang, C.; Li, K.; Ding, Y.; Yunnan Zhiwu Yanjiu Zengkan, Suppl. 3, 13–23, 1990 discloses (25S) - hecogenin cellobioside. "Determination of the Absolute Configuration of a Secondary Hydroxy Group in a Chiral Secondary Alcohol Using Glycosidation shifts in Carbon-13 NMR Spectroscopy", Seo, S.; Tomita, Y.; Tori, K.; Yoshimura, Y.; J. Am. Chem. Soc., 100(11), 3331–3339, 1978 discloses smilagenin β-glucoside and smilagenin α-glucoside. "Steroid Glycosides from Asparagus Officinalis", Lazurevskii, G. V.; Goryanu, G. M.; Kintya, P. K.; Dokl. Akad. Nauk. SSSR, 231(6), 1479–81, 1976 discloses sarsasapogenin β-glucoside.

Another steroidal glycoside having superior hypocholesterolemic activity is disclosed in commonly assigned U.S. patent application Ser. No. 07/904,914 filed Jun. 26, 1992. The application discloses the dihydrate of (3β,5α,25R)-3-[(β-D-cellobiosyl)oxy]spirostan-11-one and it's use as a hypocholesterolemic agent and antiatheroscelerosis agent.

SUMMARY OF THE INVENTION

One aspect of this invention is directed to a crystalline monohydrate of a spirostanyl glycoside that is useful as a hypocholesterolemic or antiatherosclerosis agent. The crystal has the formula

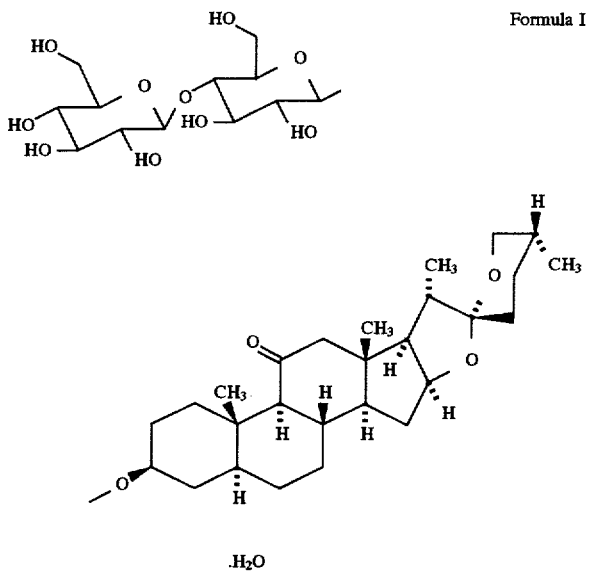

Formula I

.H₂O

Another aspect of this invention is a crystalline spirostanyl glycoside having the following X-ray diffraction d-spacing:

| d-spacing of 20 largest peaks |
|---|
| 23.74 |
| 15.78 |
| 11.82 |
| 9.48 |
| 7.90 |
| 6.77 |
| 6.34 |
| 6.26 |
| 5.91 |
| 5.75 |
| 5.61 |
| 4.72 |
| 4.61 |
| 4.13 |
| 4.00 |
| 3.91 |
| 3.64 |
| 3.38 |
| 2.63 |
| 2.49 |

Preferably, the crystalline spirostanyl glycoside having the above-d-spacing is a monohydrate.

Another aspect of this invention is a crystalline spirostanyl glycoside having the X-ray diffraction pattern of FIG. 1.

Yet another aspect of this invention is directed to pharmaceutical compositions for the control of hypercholesterolemia or atherosclerosis in mammals which comprise a crystalline compound of the Formula I and a pharmaceutically acceptable carrier. Such pharmaceutical compositions can comprise the crystalline compound of Formula I having the X-ray diffraction d-spacing shown above or the X-ray diffraction pattern of FIG. 1.

Yet another aspect of this invention is directed to a method for controlling hypercholesterolemia or atherosclerosis in a mammal by administering to a mammal suffering from hypercholesterolemia or atherosclerosis a hypercholesterolemia or atherosclerosis controlling amount of a crystalline compound of Formula I.

Yet another aspect of this invention is directed to a process for preparing a crystalline compound of Formula I. The process comprises crystallization from a suitable solvent, preferably methanol. In a preferred aspect of this process (3β,5α,25R)-3-[(β-D-cellobiosyl)oxy]spirostan-11-one is slurried in sufficient methanol for a sufficient time to provide, upon cooling, (3β,5α,25R)-3-[(β-D-cellobiosyl)oxy]spirostan-11-one monohydrate.

Thus this invention makes a significant advance in the art by providing a thermodynamically stable crystalline form of (3β,5α,25R)-3-[(β-D-cellobiosyl)oxy]spirostan-11-one. The attainment of a stable crystalline form facilitates the development and regulatory review of the compound. In addition, the crystalline form has superior handling and formulation (e.g., tabletting) characteristics. In comparison, the amorphous, or substantially amorphous, compound has a sticky clay-like consistency that makes it extremely difficult to filter.

The compound of Formula I is herein defined as the single enantiomer having the absolute stereochemistry depicted in Formula I.

Other features and advantages will be apparent from the specification and claims and from the accompanying drawing which illustrates an embodiment of the invention.

DETAILED DESCRIPTION OF THE INVENTION

Figure 1:
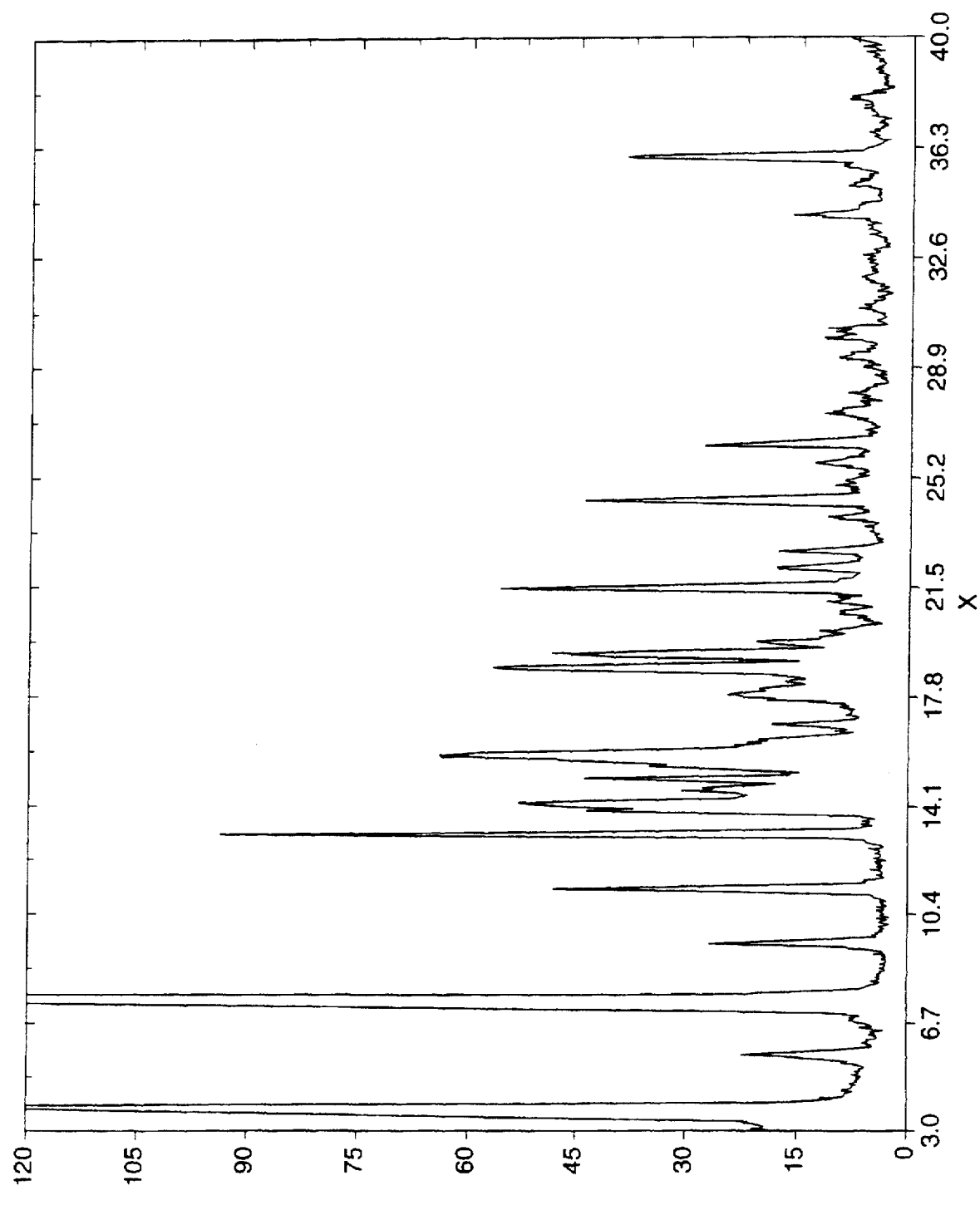
FIG. 1 illustrates an X-ray diffraction pattern of a preferred crystal of this invention.

Typically, at ambient conditions (e.g., 23° C.; 50% relative humidity) the desired crystalline compound of Formula I is a monohydrate. However, the crystalline compound may also be described as a nonstoichiometric hydrate, because crystals have been isolated which contain varying amounts of water depending upon how the crystalline material was dried and the relative humidity to which the crystalline material was exposed. Thus, although the monohydrate is the "normal" more stable state, the monohydrate can gain or lose water depending upon the relative humidity. These relative changes in the amount of water, from about 0.5 to about 2 molar equivalents, do not appear to alter the crystalline structure as evidenced by the powder X-ray diffraction pattern. For example, at 62% relative humidity the crystal can "contain" 4.5% water which is consistent with a dihydrate, and yet the X-ray diffraction pattern is consistent with the desired crystalline form. It may be that even the anhydrous compound can exhibit the desired crystalline structure as evidenced by the X-ray diffraction pattern. Thus, the desired crystal may be described as hygroscopic. A clearer understanding of this invention may be had by reference to FIG. 1 which illustrates a powder X-ray diffraction pattern of the desired crystal. In FIG. 1 intensity (Y) in cps is graphed against two theta (X) in degrees.

Substantially pure (less than about 5% impurities other than water) amorphous(3β,5α,25R)-3-[(β-D-cellobiosyl)oxy]spirostan-11-one (e.g., dihydrate, monohydrate) is converted to the desired crystalline form by slurrying the amorphous material in a suitable solvent (although clearly the conversion to the desired crystalline phase involves the dissolution of the amorphous material and precipitation of the desired crystalline form), preferably methanol or methanol-water, (as described below the water may be up to 10% of the compound weight) followed by crystallization. Preferably the amorphous starting material has less than about 10% by weight water and it is especially preferred that it has about 1 to about 4% by weight water. Typically, some part of the water becomes incorporated in the crystal as the hydrate. Alternatively, the crystallization may be performed under anhydrous conditions and the hydrate readily forms upon exposure to ambient humidity. Preferably, the concentration of compound to solvent is about 1 to 100 to about 1 to 10% by weight/volume. It is especially preferred that the concentration is from about 1 to 100 to about 4 to 100%. Preferably, the dissolution temperature varies from ambient (e.g., 17° C. to 30° C.) to reflux, with temperatures of 60° C. to reflux being more efficient. Typically the elevated temperatures are maintained for about 8 to 24 hours. If elevated temperatures are used for dissolution the resulting suspension is allowed to cool to ambient temperature and the crystals are granulated for about 12 to 60 hours and then collected by conventional means, preferably filtration and vacuum drying.

Typically, the crude (3β,5α,25R)-3-[(β-D-cellobiosyl)oxy]spirostan-11-one formed by the deacetylation (as described below in Preparation 1) is purified by a reprecipitation from a suitable solvent prior to the above preparation of the desired crystal. Preferably, the solvent is acetonitrile, methylene chloride, tetrahydrofuran, a $C_1$–$C_5$ ketone, a $C_1$–$C_4$ organic acid or a $C_1$–$C_4$ alcohol, alone or in combination with from 0 to 60% by weight water. It is especially preferred that the solvent is n-propanol/water in a ratio of about 50/50 to about 90/10 by weight. Typically the concentration of compound to solvent is about 1 to 100 to about 5 to 100% by weight/volume, preferably about 1 to 100 to about 1 to 10%. Generally, the crude deacetylation product (having substantial amorphous character) is mixed with the desired solvent(s), heated (although ambient temperatures suffice), preferably to reflux, for about 10 to 60 minutes and the insoluble material (impurities) filtered off by conventional methods of filtration (e.g., with the aid of diatomaceous earth). The solution is allowed to cool and the resulting suspension is collected by filtration.

(3β,5α,25R)-3-[(β-D-cellobiosyl)oxy]spirostan-11-one is prepared according to the methods disclosed in commonly assigned U.S. patent application Ser. No. 07/904,914 filed Jun. 26, 1992 (the disclosure of which is hereby incorporated by reference).

In particular, the claimed compound may be prepared as follows:

(3β,5α,25R)-3-[(heptaacetyl-β-D-cellobiosyl)oxy]spirostan-11-one is deacetylated by combination with a nucleophilic base such as sodium methoxide or potassium cyanide in a solvent such as methanol, tetrahydrofuran, n-propanol or mixtures thereof at elevated temperatures of about 40° C. to 100° C. (typically at reflux) and pressures of 0.5 psi to about 50 psi (typically ambient) for about 0.25 hour to about three hours to give (3β,5α,25R)-3-[(β-D-cellobiosyl)oxy]spirostan-11-one.

(3β,5α,25R)-3-[(heptaacetyl-β-D-cellobiosyl)oxy]spirostan-11-one is prepared by coupling heptaacetyl-β-D-cellobiosyl bromide and (3β,5α,25R)-3-hydroxyspirostan-11-one in a non-protic, anhydrous reaction inert solvent (e.g., acetonitrile) at a temperature of about 20° C. to about 100° C. for about 0.5 to about 12 hours in the presence of 0.5 to about 4 equivalents zinc fluoride.

The starting materials of the above described reactions (e.g., peracetylated sugar halide) are readily available or can be easily synthesized by those skilled in the art using conventional methods of organic chemistry. In particular, (3β,5α,25R)-3-hydroxyspirostan-11-one is available from Aldrich Chemical Company, Milwaukee, Wis. or Steraloids Inc., Wilton, N.H. In addition, in general, preparation methods for (3β,5α,25R)-3-hydroxyspirostan-11-one may be found in L. F. Fieser and M. Fieser, Steroids, Reinhold. Publ. Corp., New York, 1959 and references therein, however, the following text provides specific guidance.

(3β,5α,25R)-3-hydroxyspirostan-11-one may be prepared by diacetylating (3β,5α,25R)-3,12-dihydroxyspirostan-11-one using the procedure described in J. Chem. Soc., 1956, 4330 and reducing the product with calcium and ammonia using the procedure described in J. Chem. Soc. 1956, 4334. (3β,5α,25R)-3,12-dihydroxyspirostan-11-one may be prepared by monobrominating hecogenin using a procedure described in U.S. Pat. No. 3,178,418 (the disclosure of which is hereby incorporated by reference) followed by hydrolysis according to the procedure described in J. Chem. Soc. 1956, 4330.

The compound of Formula I which has been obtained and has asymmetric carbon atoms can be separated into its diastereomers on the basis of their physical chemical differences by methods known per se, for example, by chromatography and/or fractional crystallization.

The compound of this invention is a potent inhibitor of cholesterol absorption and thus is adapted to therapeutic use as a hypercholesterolemia controlling agent in mammals, particularly humans. Since hypercholesterolemia is closely related to the development of generalized cardiovascular, cerebral vascular or peripheral vascular disorders, secondarily this compound prevents the development of atherosclerosis particularly arteriosclerosis.

The hypercholesterolemia controlling activity of this compound may be demonstrated by methods based on standard procedures. For example, the in vivo activity of this compound in inhibiting intestinal absorption of cholesterol may be determined by the procedure of Melchoir and Harwell (J. Lipid Res., 1985, 26, 306–315).

Activity can be determined by the amount of hypocholesterolemic agent that reduces the cholesterol absorption, relative to the control, in male golden Syrian hamsters. Male golden Syrian hamsters are administered either a cholesterol-free diet (control animals) or a diet supplemented with 1% cholesterol and 0.5% cholic acid for 4 days. The following day the animals are fasted for 18 hours, then administered a 1.5 mL oral bolus of water containing 0.25% methylcellulose, 0.6% Tween 80 and 10% ethanol (control animals) or an oral bolus that contains, in addition, the desired concentration of the compound to be tested. Immediately following bolus administration, the animals receive a second 1.5 mL oral bolus of liquid hamster diet containing 1% [$^3$H] cholesterol (2.0 µCi/animal; 210 dpm/nmol) and 0.5% cholic acid, and are fasted for an additional 24 hours. At the end of this second fasting period animals are sacrificed livers, are excised, saponified and aliquots are decolorized by addition of hydrogen peroxide, and assessed for radioactivity. Total hepatic radioactivity is calculated based on measured liver weights. The degree of cholesterol absorption is expressed as a percentage of the total radioactivity administered as an oral bolus that is present in the liver 24 hours following bolus administration.

Anti-atherosclerosis effects of the compounds can be determined by the amount of agent that reduces the lipid deposition in the rabbit aorta. Male New Zealand white rabbits are fed a diet containing 0.4% cholesterol and 5% peanut oil for 1 week (meal-fed once a day). After 1 week some of the rabbits (the control group) continue with the diet and the remainder receive the diet supplemented with the desired concentration of the compound to be tested. After 8.5 weeks, drug treatment is discontinued and the animals are maintained on the cholesterol containing diet for an additional 2 weeks and then switched to a cholesterol free diet for 5 weeks. The animals are sacrificed, and the aortas removed from the thoracic arch to the branch of the iliacs. The aortas are cleaned of adventitia, opened longitudinally and then stained with Sudan IV as described by Holman et al. (Lab. Invet. 1958, 7, 42–47). The percent of the surface area stained is quantitated by densitometry using an Optimas Image Analyzing System (Image Processing Systems). Reduced lipid deposition is indicated by a reduction in the percent surface area stained in the drug treated group in comparison with the control rabbits.

Administration of the compound of this invention can be via any method which delivers the compound to the intestinal lumen. These methods include oral routes, intraduodenal routes, etc.

The amount of steroidal glycoside administered will, of course, be dependent on the subject being treated, on the severity of the affliction, on the manner of administration and on the judgement of the prescribing physician. However, an effective dosage is in the range of 0.71 to 200 mg/kg/day, preferably 2 to 50 mg/kg/day, most preferably 2 to 7 mg/kg/day. For an average 70 kg human, this would amount to 0.05 to 14 g/day, preferably 0.14 to 3.5 g/day, most preferably 0.14 to 0.5 g/day.

For oral administration, which is preferred, a pharmaceutical composition can take the form of solutions, suspensions, tablets, pills, capsules, powders, sustained release formulations and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition or formulation to be administered will contain a quantity of a compound according to the invention in an anti-hypercholesterolemia or anti-atherosclerosis effective amount.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing the steroidal glycoside, and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those skilled in this art. For examples, see Remington's Pharmaceutical Sciences., Mack Publishing Company, Easter, Pa., 15th Edition (1975).

EXAMPLE 1

Crystalline (3β,5α,25R)-3-[(β-D-cellobiosyl)oxy] spirostan-11-one

In a paddle stirred, three neck, round bottom flask, the undried cake from the partial crystallization (see Preparation A below) (vide supra) was suspended in 500 ml of methanol. The suspension contained 2.5% water by Karl Fischer analysis. The stirred suspension was heated to reflux for 16 hours, cooled to ambient temperature, and granulated for 48 hours. The titled compound was isolated by filtration and vacuum dried to yield 16.1 g (81% recovery). Powder X-ray diffraction of the sample demonstrated that a desired crystalline form of the titled compound had been isolated.

A similarly prepared material was analyzed as follows. Thermal gravimetric analysis (heating rate 30° C./min.) shows a 1.8% weight loss at 100° C. and a 3.0% weight loss at 300° C. The water content as determined by Karl Fischer titration was 1.4%. Differential scanning calorimetry (heating rate, 20° C./min) on the dried material gives 2 small endotherms (at about 211° and 295° C.), followed by decomposition.

Anal Calcd. for $C_{39}H_{62}O_{14}1H_2O$: C 60.61; H 8.35 Found: C 60.81; H 8.32

Preparation A (3β, 5α, 25R)-3-[(β-D-cellobiosyl)oxy]spirostan-11-one

DEACETYLATION

A mixture of (3β,5α,25R)-3-[(heptaacetyl-β-D-cellobiosyl)oxy]spirostan-11-one (6.57 g, 6.26 mmol), sodium methoxide (68 mg, 1.25 mmol), methanol (35 mL) and tetrahydrofuran (75 mL) was heated to reflux for 1 hour, followed by stirring at room temperature for 12 hours. A white precipitate formed within 30 minutes. The final suspension was concentrated in vacuo to give 6.0 g of crude product. This material was purified by flash chromatography (eluent:chloroform followed by 8:2 chloroform:methanol) to give 2.71 g (57% yield) of the title compound.

$^1$H NMR (DMSO-$d_6$) δ: 5.22 (d, J=5Hz, 1H); 5.00 (m, 3H); 4.64 (s, 1H); 4.58 (t, J=5 Hz, 1H); 4.54 (t, J=6Hz, 1H); 4.34 (q, J=8 Hz, 1H); 4.27 (d, J=8Hz, 1H); 4.23 (d, J=8 Hz, 1H); 3.68–2.94 (m, 15 H); 2.34 (m, 2H); 2.08–0.81 (m, 23H); 0.92 (s, 3H); 0.86 (d, J=7 Hz, 3H); 0.72 (d, J=6 Hz, 3H); 0.59 (s, 3H). DEPT $^{13}$C NMR (DMSO-$d_6$) δ: 210.4 (s), 108.8 (s), 103.6 (d), 100.6 (d), 81.1 (d), 80.6 (d), 77.2 (d), 76.9 (d), 76.5 (d), 75.5 (d), 75.1 (d), 73.7 (d), 73.6 (d), 70.5 (d), 66.4 (t), 63.5 (d), 61.5 (t), 60.9 (t), 50.5 (d), 57.1 (t), 54.7 (d), 44.3 (s), 44.1 (d), 41.7 (d), 36.8 (d), 35.6 (t), 35.2 (s), 34.0 (t), 32.6 (t), 31.3 (s), 30.2 (d), 29.2 (t), 28.9 (t), 28.2 (t), 17.5 (q), 17.3 (q), 14.8 (q), 12.3 (q). IR (KBr): 3407 (s), 1700 (m) cm$^{-1}$. High resolution FAB MS (m/e): calculated for $C_{39}H_{62}O_{14}Na$ 777.4037, found 777.4108. Analysis: calc. for $C_{39}H_{62}O_{14}\cdot 2H_2O$, C 59.22 H 8.41; found C 59.48, H 8.48. MP: >300° C.

A paddle stirred, three neck, round bottom flask was charged with 20 g of deacetylation product made according to the above reaction, 600 mL of n-propanol, and 400 mL of water. This suspension was heated to reflux at which time a solution formed. To this solution was charged 2.0 g of diatomaceous earth. While maintaining reflux temperature, the insolubles were removed by filtration (spec free filtration). The filtrate was atmospherically distilled until a total volume of 600 ml had been achieved then cooled to ambient temperature. Karl Fischer assay of this suspension reflected it contained 40.5% water. The resulting suspension was granulated for one hour and a partially crystallized product (intermediate phase) was collected by filtration. Although partially crystallized, the product did not display the desired X-ray diffraction pattern.

Preparation B (3β,5α,25R)-3-[(Heptaacetl-β-D-cellobiosyl)oxy]-spirostane-11-one

ZINC FLUORIDE PROMOTED COUPLING OF FREE SPIROSTANE

A suspension of (3β,5α,25R)-3-hydroxyspirostan-11-one (3.0 g, 6.97 mmol) and anhydrous zinc fluoride (2.88 g, 27.9 mmol) in dry acetonitrile (175 mL) was dried by removal of 75 mL of acetonitrile by distillation. The suspension was allowed to cool, heptaacetyl-β-D-cellobiosyl bromide (9.75 g, 13.9 mmol) was added and the resulting suspension was heated to 65° C. for 3 hours. After cooling to room temperature, methylene chloride (150 mL) was added, the suspension was stirred for 10 minutes and filtered. The filtrate was concentrated in vacuo to give 10 g of crude product. This material was dissolved in 8:2 chloroform:methanol, preadsorbed on silica gel and purified by flash chromatography (eluent: 1:1 ethyl acetate:hexane followed by pure ethyl acetate) to give 6.81 g (93% yield) of the title material.

$^1$H NMR (CDCl$_3$) δ: 5:11 (complex, 2 H); 5.04 (t, J=9 Hz, 1H); 4.90 (t, J=9 Hz, 1H); 4.83 (t, J=8 Hz, 1H); 4.49 (complex, 4H); 4.34 (dd, J=4.5 & 12.5 Hz, 1H); 4.04 (t, J=13 Hz, 1H); 4.03 (t, J=11 Hz, 1H); 3.72 (t, J=9.5 Hz, 1H); 3.65 (m, 1H); 3.56 (m, 1H); 3.45 (m, 1H); 2.47 (m, 1H); 2.22 (s, 2H); 2.08 (s, 3H); 2.06 (s, 3H); 2.00 (s, 6H); 1.99 (s, 6H); 1.96 (s, 3H); 2.00–1.00 (m, 22H); 0.98 (s, 3H); 0.92 (d, J=7 Hz, 3H); 0.77 (d, J=7 Hz, 3H); 0.68 (s, 3H). DEPT $^{13}$C NMR (CDCl$_3$) δ: 209.9 (s), 170.5 (s), 170.3 (s), 170.2 (s), 169.9 (s), 169.8 (s), 169.5 (s), 169.3 (s), 169.0 (s), 109.2 (s), 100.8 (d), 99.4 (d), 90.0 (s), 80.6 (d), 79.4 (d), 76.6 (d), 75.3 (s), 72.9 (d), 72.6 (d), 72.5 (d), 71.9 (d), 71.8 (d), 71.6 (d), 67.8 (s), 66.9 (t), 64.4 (d), 62.1 (t), 61.5 (t), 60.8 (s), 60.7 (d), 57.6 (t), 55.7 (d), 44.8 (d), 44.3 (s), 41.8 (d), 36.9 (d), 35.6 (t), 35.2 (s), 34.1 (t), 32.7 (t), 31.3 (t), 31.2 (t), 30.2 (d), 29.0 (t), 28.7 (t), 28.0 (t), 20.9 (q), 20.7 (q), 20.6 (q), 20.5 (q), 20.5 (q), 17.1 (q), 17.0 (q), 14.2 (q), 12.0 (q). IR (KBr): 1756 (s), 1706 (m) cm$^{-1}$. MS (m/e): 1049 (M+H). Analysis: calc. for C$_{53}$H$_{76}$O$_{21}$·H$_2$O, C 59.65, H 7.37; found C 59.86, H 7.25. MP: 210°–212° C.

Preparation C (3β,5α,12β,25R)spirostan-3,12-diol-11-one (3β,5α,11β,25R)-11-bromospirostan-3-ol-12-one:

A glass lined reactor was charged with 50 gallons of methanol then subsurface sparged with hydrochloric acid gas until 7.7 Kg (5.0 eq) were charged. Upon completion of this sparge, the reactor was charged with 18.8 Kg (42.2 mole) of (3β,5α,25R)spirostan-3-ol-12-one (hecogenin), 50 gallons of methanol and 10 gallons of methylene chloride. This mixture was cooled to 10° C. and a solution of 8.4 Kg bromine (52.7 mole, 1.25 eq) in 10 gallons of methylene chloride was added over 2 hours while a pot temperature of approximately 10° C. was maintained. Once the addition was complete the reaction was allowed to warm to room temperature and was stirred for 2 hours. TLC at this point indicated complete reaction.

The reaction was diluted with 50 gallons of water and stirred for 10 minutes. After separation of layers, the aqueous layer was extracted twice with 30 gallons of methylene chloride. The three combined organic extracts were washed twice with 30 gallons of water, once with 30 gallons of saturated brine, then dried using 7.0 Kg of magnesium sulfate. The drying agent was removed by filtration on a 30 inch Lapp followed by two 3 gallon methylene chloride washes. The filtrate and washes combined were atmospherically distilled to a 7 gallon total volume. Two 10 gallon methanol charges were made followed by continued distillation. When a final volume of <10 gallons had been reached the mixture was cooled to room temperature. The resulting suspension was granulated for 2 hours, filtered on a 30 inch Lapp, and the filter cake was washed twice with 3 gallons of methanol. Vacuum drying the filter cake at 45°–50° C. yielded 12.6 Kg (58.6% yield) of the titled compound.

(3β,5α,12β,25R)spirostan-3,12-diol-11-one:

A glass lined reactor was charged with 12.4 Kg of (3β,5α,11β,25R)-11-bromospirostan-3-ol-12-one (24.34 mole), 33 gallons of t-butanol, 33 gallons of water and 7.5 Kg (189 mole, 7.75 eq) of sodium hydroxide pellets. The reaction was heated to reflux over 1.5 hours, maintained at reflux for 4.5 hours (pot temperature was 83° C.), then cooled to room temperature. TLC at this point indicated complete reaction.

The reaction was distilled to remove the t-butanol. This was accomplished both by vacuum and atmospheric distillation. During the concentration, two 32.5 gallon charges of water were added. Once the t-butanol had been removed, the aqueous suspension was cooled to room temperature and granulated for 2 hours. The suspension was filtered on a 30 inch Lapp, washed twice with 3 gallons of water, and the filter cake was air dried at 60° C. This afforded 11.1 Kg of the titled compound.

Preparation D (3β,5α,25R)spirostan-3-ol-11-one (3β,5α,12β,25R)-3,12-diacetoxyspirostan-11-one:

A glass lined reactor was charged with 26 gallons of pyridine, 26 gallons of acetic anhydride and 11.0 Kg of (3β,5α,12β,25R)spirostan-3,12-diol-11-one (preparation C). This mixture was refluxed for 2 hours (pot temperature 128° C.) and allowed to cool to room temperature. The reaction was vacuum distilled to a total volume of 15 gallons (pot temperature approximately 45° C. during distillation). The suspension was diluted with 25 gallons of acetic acid and further vacuum distilled to a 15 gallon total volume (pot temperature at end approximately 80° C.). The mixture was diluted with 87 gallons of water and cooled to room temperature. After 5 hours of granulation, the titled compound was isolated by filtration on a 30 inch Lapp followed by two 3 gallon water washes. The filter cake was dried at 60° C. under vacuum to yield 12.2 Kg (93.3%).

(3β,5α,25R)spirostan-3-ol-11-one:

A stainless steel reactor was cooled to −80° C. by passing liquid nitrogen through internal coils. Ammonia was added to the reactor until 54.5 Kg (80 liters, 3,200 mole, 170 eq) had been charged.

At the same time that the ammonia charge was commencing a glass lined reactor was charged with 10.0 Kg of (3β,5α,12β,25R)-3,12-diacetoxyspirostan-11-one 18.84 mole) and 40 gallons of THF. This solution was atmospherically distilled until a 26 gallon total volume had been reached.

At the completion of the ammonia charge, 2.8 Kg of calcium turnings (69.0 gram atoms, 3.7 eq) were added over 30 minutes while maintaining a pot temperature of −50° C. At the completion of this addition the THF solution of (3β,5α,12β,25R)-3,12-diacetoxyspirostan-11-one was added over 20 minutes (pot temperature at the end of the addition was −35° C.) followed by a 1.0 gallon THF rinse. The reaction mixture was stirred for 30 minutes at −35° C. to −40° C. While the reaction was at −35° C. to −40° C., 3.33 liters of bromobenzene (4.98 Kg, 31.7 mole, 1.68 eq) were added followed by 3.33 liters of water.

After this addition the distillation of ammonia from the reactor was initiated. This distillation was directed to a water scrubber. Once all of the ammonia had been removed, the reaction (now at 24° C.) was transferred to a glass lined reactor followed by a 4 gallon THF rinse. The solution and rinse combined were vacuum distilled to a thick oil. To this was added 35 gallons of methanol and 3.3 Kg (59 mole) of potassium hydroxide pellets. This mixture was heated at reflux for 1 hour, cooled, then 10 liters of acetic acid and 44 gallons of water were charged. This suspension was further cooled to room temperature and granulated for 1 hour. The titled compound was isolated by filtration on a 30 inch Lapp followed by a 5 gallon 3:1 water/methanol wash. Vacuum drying at 55° C. yielded 7.05 Kg (86.9%).

It should be understood that the invention is not limited to the particular embodiments shown and described herein, but that various changes and modifications may be made without departing from the spirit and scope of this novel concept as defined by the following claims.

We claim:

1. A crystalline monohydrate of a spirostanyl glycoside having the formula

Formula I

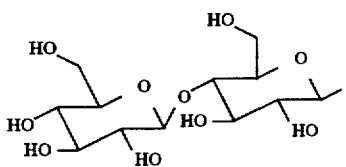

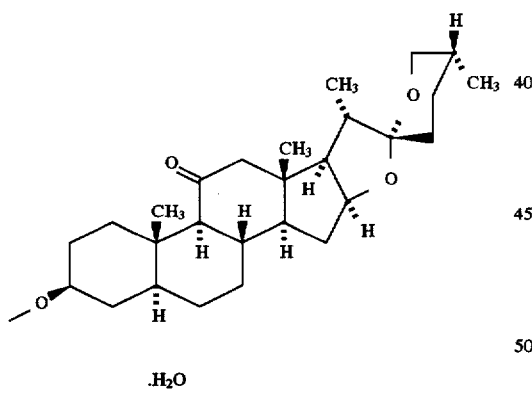

.H₂O

2. A pharmaceutical composition for the control of hypercholesterolemia or atherosclerosis in mammals which comprises a crystalline monohydrate of a spirostanyl glycoside having the formula Formula I

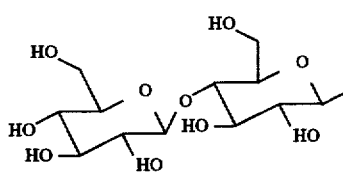

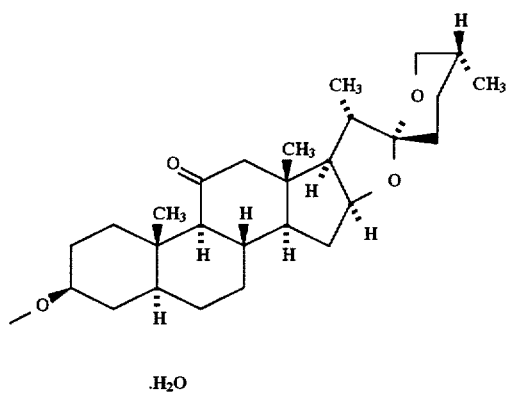

.H₂O and a pharmaceutically acceptable carrier.

3. The pharmaceutical composition as recited in claim 2 wherein the crystalline monohydrate has the X-ray diffraction pattern of FIG. 1.

4. A method for controlling hypercholesterolemia or atherosclerosis in a mammal comprising administering to a mammal suffering from hypercholesterolemia or atherosclerosis a hypercholesterolemia or atherosclerosis controlling amount of a crystalline monohydrate of a spirostanyl glycoside having the formula Formula I

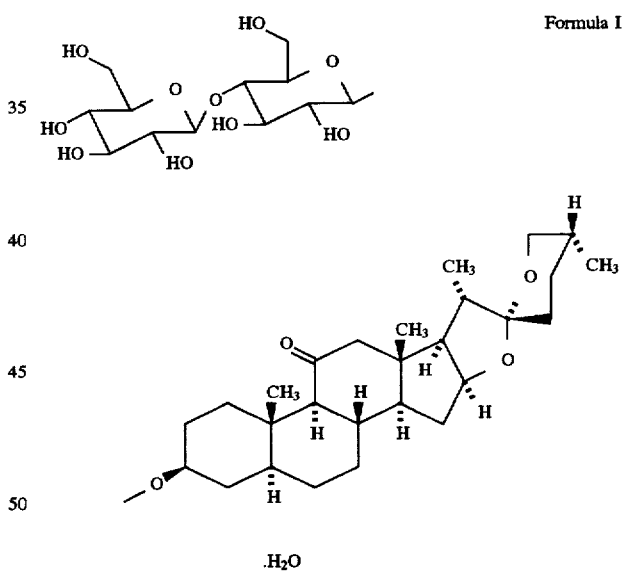

.H₂O

5. A process for preparing a crystalline steroidal glycoside comprising: slurrying (3β,5α,25R)-3-[(β-D-cellobiosyl)oxy]spirostan-11-one in methanol and allowing crystalline (3β,5α,25R)-3-[(β-D-cellobiosyl)oxy]spirostan-11-one monohydrate to form.

6. The process as recited in claim 5 wherein the methanol solution is heated and upon cooling the crystals form.

* * * * *